(12) United States Patent
Sakashita et al.

(10) Patent No.: US 9,791,465 B2
(45) Date of Patent: Oct. 17, 2017

(54) AUTOMATIC ANALYZER

(71) Applicant: HITACHI HIGH-TECHNOLOGIES CORPORATION, Tokyo (JP)

(72) Inventors: Yukinori Sakashita, Tokyo (JP); Katsuhiro Kambara, Tokyo (JP); Yoshihiro Yamashita, Tokyo (JP)

(73) Assignee: Hitachi High-Technologies Corporation, Tokyo (JP)

(*) Notice: Subject to any disclaimer, the term of this patent is extended or adjusted under 35 U.S.C. 154(b) by 0 days.

(21) Appl. No.: 14/379,350

(22) PCT Filed: Feb. 19, 2013

(86) PCT No.: PCT/JP2013/054033
§ 371 (c)(1),
(2) Date: Aug. 18, 2014

(87) PCT Pub. No.: WO2013/125536
PCT Pub. Date: Aug. 29, 2013

(65) Prior Publication Data
US 2015/0037214 A1 Feb. 5, 2015

(30) Foreign Application Priority Data
Feb. 22, 2012 (JP) .................................. 2012-036632

(51) Int. Cl.
*G01N 35/10* (2006.01)
*G01N 35/00* (2006.01)
(Continued)

(52) U.S. Cl.
CPC ....... *G01N 35/00584* (2013.01); *G01N 35/08* (2013.01); *G01N 35/1004* (2013.01);
(Continued)

(58) Field of Classification Search
CPC .. G01N 35/08; G01N 35/085; G01N 35/1004; G01N 2035/1062
See application file for complete search history.

(56) References Cited

U.S. PATENT DOCUMENTS

| 6,066,298 A * | 5/2000 | Fukunaga | G01N 1/38 134/170 |
| 2011/0232769 A1* | 9/2011 | Nichogi | G01N 35/025 137/3 |
| 2013/0125671 A1* | 5/2013 | Sakashita | G01N 35/1081 73/863.01 |

FOREIGN PATENT DOCUMENTS

| JP | 07-248330 A | 9/1995 |
| JP | 10-300752 A | 11/1998 |

(Continued)

OTHER PUBLICATIONS

International Preliminary Report on Patentability received in International Application No. PCT/JP2013/054033 dated Sep. 4, 2014.

*Primary Examiner* — P. Kathryn Wright
(74) *Attorney, Agent, or Firm* — Mattingly & Malur, PC

(57) ABSTRACT

The automatic analyzer includes a suction nozzle; a liquid transfer syringe; a suction channel which connects the suction nozzle and the liquid transfer syringe; a flow cell which is arranged in the middle of the suction channel; a detector for sample analysis which is arranged in the flow cell; a reaction auxiliary liquid vessel and a cleaning liquid vessel which store liquids to be sucked in by the suction nozzle; means for supplying a diluting fluid to the vessels; a cleaning tank for dumping liquid remaining in the vessels; and a controller for supplying the diluting fluid to the vessels when the remaining liquid is discharged from the vessels and thereafter having the diluted remaining liquid sucked into the flow cell via the suction nozzle and having the sucked remaining liquid discharged to the cleaning tank.

7 Claims, 10 Drawing Sheets

(51) Int. Cl.
*G01N 35/08* (2006.01)
*G01N 35/04* (2006.01)
*G01N 35/02* (2006.01)

(52) U.S. Cl.
CPC ... *G01N 35/025* (2013.01); *G01N 2035/0413* (2013.01); *G01N 2035/0443* (2013.01); *G01N 2035/1062* (2013.01)

(56) References Cited

FOREIGN PATENT DOCUMENTS

| | | | |
|---|---|---|---|
| JP | 11-242032 | A | 9/1999 |
| JP | 2000-065833 | A | 3/2000 |
| JP | 2008-058127 | A | 3/2008 |
| JP | 2009-276214 | A | 11/2009 |
| WO | 2011/155489 | A1 | 12/2011 |
| WO | 2012/011481 | A1 | 1/2012 |

\* cited by examiner

AUTOMATIC ANALYZER

TECHNICAL FIELD

The present invention relates to an automatic analyzer for detecting particular biogenic substances, chemical substances, etc. contained in a sample.

BACKGROUND ART

Automatic analyzers are used for detecting particular biogenic substances, chemical substances, etc. contained in a sample (blood, blood serum, urine, etc.) especially in the fields of medical care, biotechnology, etc. Among such automatic analyzers, there is an automatic analyzer comprising a suction nozzle, a syringe which is connected to the suction nozzle by a channel and operates to cause a liquid to be sucked into the suction nozzle, and a detector of the flow cell type which is arranged in the middle of the channel (hereinafter referred to as a "detection channel") connecting the suction nozzle and the syringe (see Patent Literature 1, for example). In this type of automatic analyzer, a reaction solution in which the sample and a reagent have undergone a reaction is sucked into the flow cell through the suction nozzle, and particular biogenic substances, chemical substances, etc. contained in the sucked reaction solution are detected by the detector.

PRIOR ART LITERATURE

Patent Literature

Patent Literature 1: JP-2008-58127-A

SUMMARY OF THE INVENTION

Problem to be Solved by the Invention

When old liquid remaining in a liquid vessel is discharged in order to replace the liquid in the liquid vessel, there are cases where the remaining liquid in the liquid vessel is sucked in by the suction nozzle and the sucked remaining liquid is discharged and dumped to a waste channel. However, in such automatic analyzers having a flow cell-type detector arranged in the detection channel, unnecessary inflow of the remaining liquid into the flow cell can have bad influence on the performance of the detector. Thus, in order to prevent the inflow of the remaining liquid into the flow cell, the amount of suction in each sucking operation is limited within the capacity of the channel from the suction nozzle to the flow cell. Consequently, the suction and the discharging have to be repeated a lot of times until the remaining liquid in the liquid vessel is discharged.

The object of the present invention, which has been made in consideration of the above-described situation, is to provide an automatic analyzer capable of quickening the replacement of liquid in each liquid vessel, shortening the analysis preparation time, and speeding up the processing.

Means for Solving the Problem

To achieve the above object, when remaining liquid is discharged from a liquid vessel for storing liquid to be sucked in by the suction nozzle, a diluting fluid is supplied to the liquid vessel and thereafter the remaining liquid is sucked into a channel connecting the suction nozzle and a liquid transfer syringe together through the suction nozzle and the sucked remaining liquid is discharged to a dumping part.

Effect of the Invention

According to the present invention, the replacement of liquid in each liquid vessel can be quickened, the analysis preparation time can be shortened, and the processing can be speeded up.

MODES FOR CARRYING OUT THE INVENTION

Figure 1:
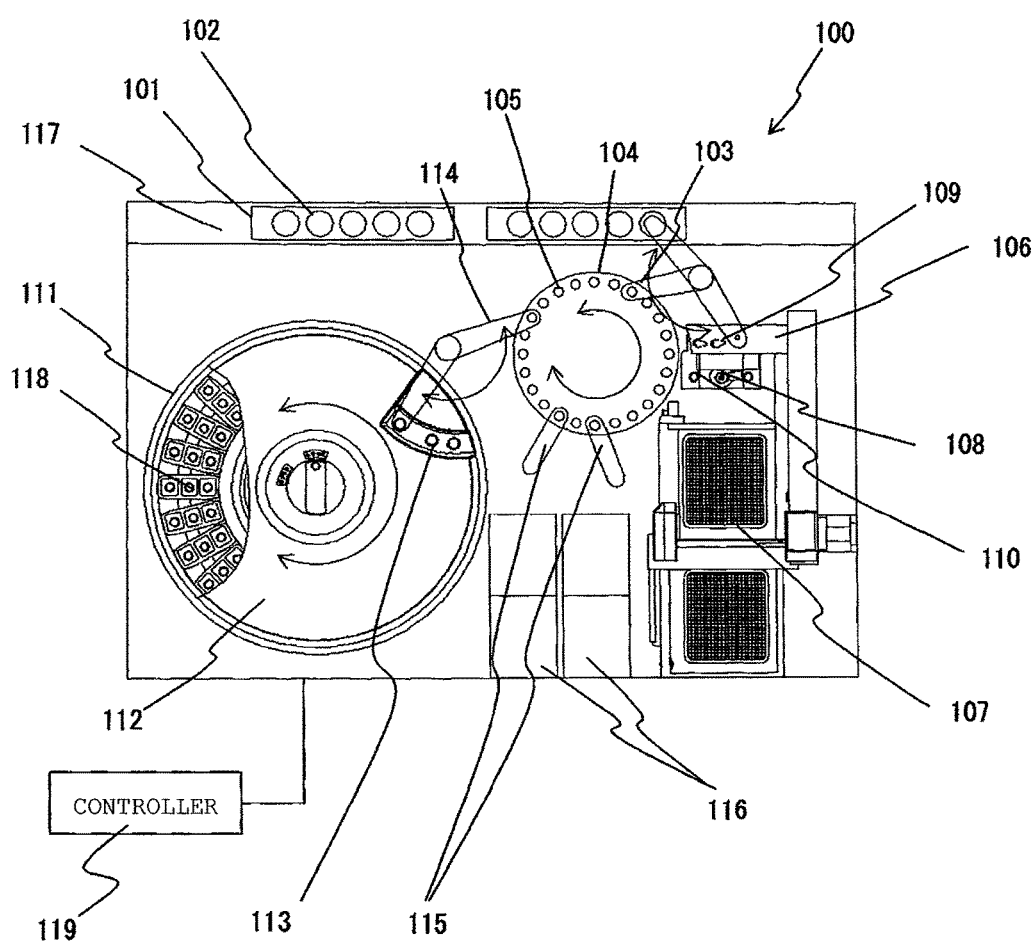
FIG. 1 is a plan view showing the overall configuration of an example of an automatic analyzer as the target of application of the present invention.

Referring now to the drawings, a description will be given in detail of preferred embodiments of the present invention.

1. First Embodiment (1) Device Configuration

FIG. 1 is a plan view showing the overall configuration of an example of an automatic analyzer as the target of application of the present invention.

The analyzer 100 comprises a rack transfer line 117 for transferring racks 101, an incubator disk 104 on which reaction vessels 105 are set, a sample dispensing tip/reaction vessel transfer mechanism 106 for transferring sample dispensing tips and the reaction vessels 105, a sample dispensing tip/reaction vessel holding member 107 for holding the sample dispensing tips and the reaction vessels 105, a reaction vessel stirring mechanism 108 for stirring the sample in the reaction vessel 105, a sample dispensing nozzle 103 for dispensing/discharging a sample, a reagent disk 111 on which reagent vessels 118 are set, a reagent dispensing nozzle 114 for dispensing/discharging a reagent, a detection unit 116 for detecting particular biogenic substances, chemical substances, etc. contained in a reaction solution in the reaction vessel 105, a reaction vessel transfer mechanism 115 for transferring the reaction vessels 105 between the incubator disk 104 and the detection unit 116, and a controller 119 for controlling the operation of the above components.

The rack transfer line 117 transfers each rack 101 to a sample dispensing position on the line for the sample dispensing nozzle 103. The rack 101 is capable of holding a plurality of sample vessels 102 storing samples. While a configuration for the line transfer of the samples is illustrated in this example, there are also cases where a disk-shaped mechanism for transferring the samples by means of rotation is arranged in the automatic analyzer.

The incubator disk 104, on which a plurality of reaction vessels 105 can be set in a circular pattern, is driven and rotated by an unshown drive unit. The incubator disk 104 is capable of transferring an intended reaction vessel 105 to a prescribed position such as the dispensing position for the sample dispensing nozzle 103.

The sample dispensing tip/reaction vessel transfer mechanism 106, capable of moving in three axial directions (X-axis direction, Y-axis direction, Z-axis direction), transfers the sample dispensing tips and the reaction vessels among prescribed positions of the sample dispensing tip/reaction vessel holding member 107, the reaction vessel stirring mechanism 108 and the incubator disk 104, a sample dispensing tip/reaction vessel discarding hole 109, and a sample dispensing tip attaching position 110.

A plurality of unused reaction vessels 105 and sample dispensing tips are set on the sample dispensing tip/reaction vessel holding member 107. The sample dispensing tip/reaction vessel transfer mechanism 106 moves to a position over the sample dispensing tip/reaction vessel holding member 107, descends, takes hold of an unused reaction vessel 105, ascends, moves to a position over a prescribed position of the incubator disk 104, descends, and sets the reaction vessel 105 on the incubator disk 104. Alternatively, the sample dispensing tip/reaction vessel transfer mechanism 106 moves to a position over the sample dispensing tip/reaction vessel holding member 107, descends, takes hold of an unused sample dispensing tip, ascends, moves to a position over the sample dispensing tip attaching position 110, descends, and sets the sample dispensing tip at the sample dispensing tip attaching position 110.

The sample dispensing nozzle 103 is capable of rotating, ascending and descending (moving vertically). The sample dispensing nozzle 103 rotates and moves to a position over the sample dispensing tip attaching position 110, and descends to the sample dispensing tip attaching position 110 so that a sample dispensing tip is attached to the tip end of the sample dispensing nozzle 103 by means of press fitting. The sample dispensing nozzle 103 having the sample dispensing tip attached thereto moves to a position over a sample vessel 102 which has been set on the rack 101, descends, and sucks in a prescribed amount of sample stored in the sample vessel 102. The sample dispensing nozzle 103 which has sucked in a sample moves to a position over the incubator disk 104, descends, and discharges the sample into an unused reaction vessel 105 held on the incubator disk 104. After finishing the sample discharge, the sample dispensing nozzle 103 moves to a position over the sample dispensing tip/reaction vessel discarding hole 109 and discards the used sample dispensing tip through the sample dispensing tip/reaction vessel discarding hole 109.

A plurality of reagent vessels 118 are set on the reagent disk 111. A reagent disk cover 112 (left part is removed imaginarily in FIG. 1) is arranged over the reagent disk 111 and the inside of the reagent disk 111 is kept at a prescribed temperature. An opening part 113 is formed in a part of the reagent disk cover 112 on the incubator disk 104's side.

The reagent dispensing nozzle 114 is capable of rotating, ascending and descending similarly to the sample dispensing nozzle 103. The reagent dispensing nozzle 114 rotates and moves to a position over the opening part 113 of the reagent disk cover 112, descends, has its tip end inserted into a prescribed reagent vessel 118, and sucks in a prescribed amount of reagent. Subsequently, the reagent dispensing nozzle 114 ascends, rotates and moves to a position over a prescribed position of the incubator disk 104, and discharges the reagent into a reaction vessel 105 storing a sample to be mixed with the reagent.

The reaction vessel 105 storing the sample and the reagent discharged thereto is moved to a prescribed position by the rotation of the incubator disk 104 and then transferred to the reaction vessel stirring mechanism 108 by the sample dispensing tip/reaction vessel transfer mechanism 106. The reaction vessel stirring mechanism 108 stirs and mixes the sample and the reagent stored in the reaction vessel 105 by giving a rotating motion to the reaction vessel 105. The reaction vessel 105 after finishing the stirring is returned to the prescribed position of the incubator disk 104 by the sample dispensing tip/reaction vessel transfer mechanism 106.

The reaction vessel transfer mechanism 115 is capable of rotating, ascending and descending similarly to the sample dispensing nozzle 103. The reaction vessel transfer mechanism 115 moves to a position over a reaction vessel 105 of which a prescribed reaction time has passed since the returning of the vessel to the incubator disk 104 after the completion of the dispensing and the stirring of the sample and the reagent, descends, takes hold of the reaction vessel 105, ascends, and transfers the reaction vessel 105 to the detection unit 116 by means of rotational transfer.

The above processes by the components of the analyzer and the operation of the detection unit 116 (explained below) are implemented by control by the controller 119.

Figure 2:
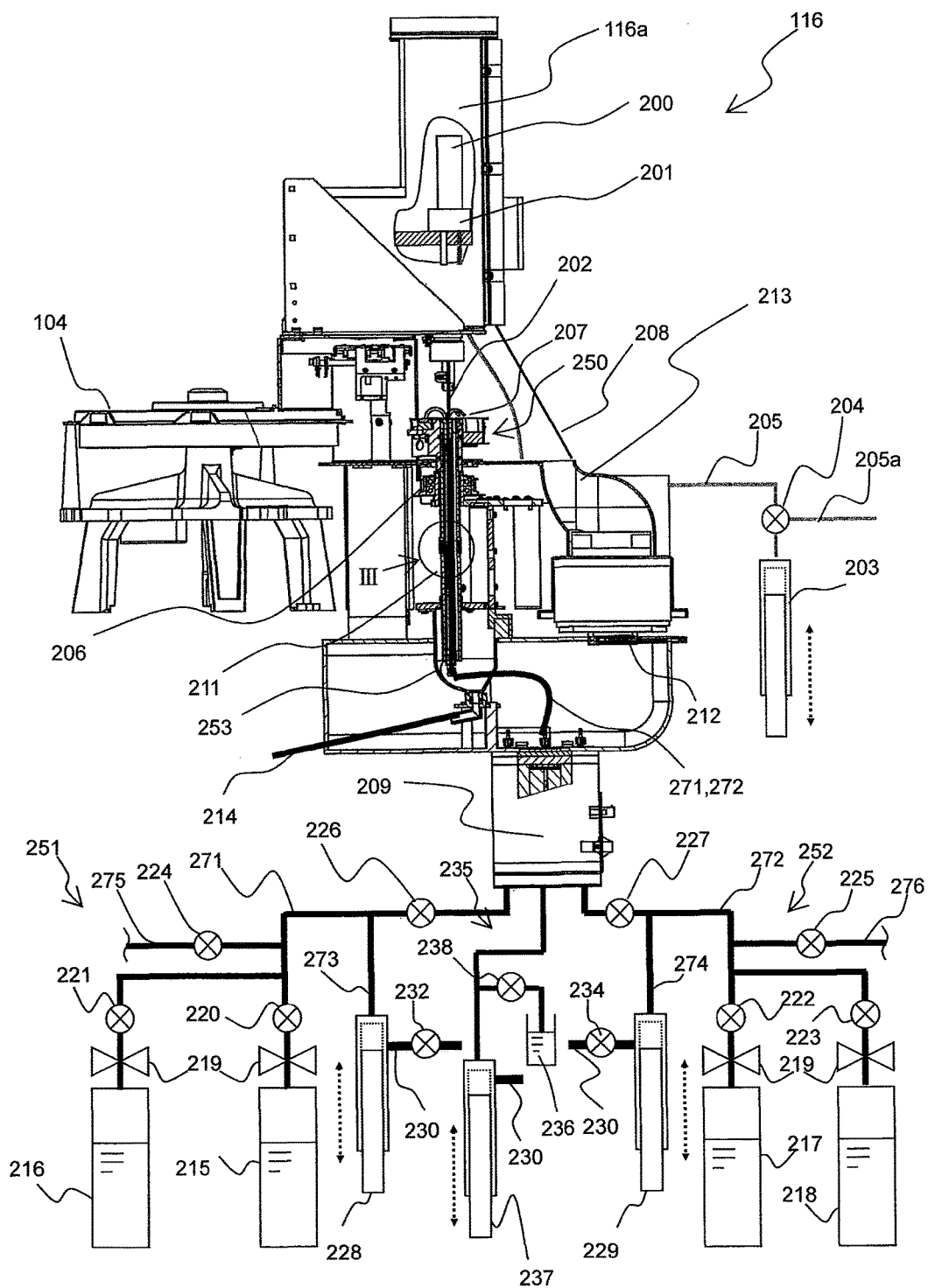
FIG. 2 is a schematic diagram showing the overall configuration of a detection unit of an automatic analyzer in accordance with a first embodiment of the present invention and components around the detection unit.

FIG. 2 is a schematic diagram showing the overall configuration of the detection unit 116 and its surroundings.

As shown in FIG. 2, the detection unit 116 includes a suction nozzle 202, a liquid transfer syringe 203, a suction channel 205 connecting the suction nozzle 202 and the liquid transfer syringe 203 together, a flow cell (detection vessel) 201 arranged in the middle of the suction channel 205, a detector 200 arranged in the flow cell 201 for analyzing the sample, and a unit body 116a storing the flow cell 201 and the detector 200. A waste channel 205a branches off from the suction channel 205. An electromagnetically-driven channel selector valve 204 is provided at the branching part of the waste channel 205a and the suction channel 205. The operation is switched between liquid transfer to the flow cell 201 and liquid transfer to the waste channel 205a (after finishing the analysis) by switching the channel selector valve 204 and operating the liquid transfer syringe 203. For example, by having the channel selector valve 204 connect the liquid transfer syringe 203 to the suction channel 205 and having the liquid transfer syringe 203 perform the suction, a certain type of liquid (reaction solution, reaction auxiliary liquid, cleaning liquid, etc.)

stored in a reservoir unit 250 (explained later) is sucked in through the suction nozzle 202 and transferred to the flow cell 201.

Incidentally, the suction nozzle 202 of the detection unit 116 in this embodiment is always fixed at a constant position, without rotating, ascending or descending like the sample dispensing nozzle 103. Thus, a liquid transfer mechanism for transferring each liquid vessel to a sucking position of the suction nozzle 202 is arranged in the lower part of the detection unit 116. Since the suction nozzle 202 of the detection unit 116 is always fixed at the constant position, deformation of the continuous channel (suction nozzle 202→flow cell 201→suction channel 205) due to the liquid suction/discharging operation of the suction nozzle 202 does not occur.

The liquid transfer mechanism includes the reservoir unit 250 for moving each liquid vessel with respect to the suction nozzle 202, an reaction auxiliary liquid supply system 251 for supplying the reaction auxiliary liquid to the reservoir unit 250, a cleaning liquid supply system 252 for supplying the cleaning liquid to the reservoir unit 250, a cleaning liquid supply system 235 for supplying a cleaning liquid for the cleaning of an overflow part 502 (explained later) to the reservoir unit 250, a liquid temperature control unit 209 for keeping the liquids supplied to the reservoir unit 250 (reaction auxiliary liquid, cleaning liquid) within a certain temperature range, and an air temperature control unit 212 for keeping the ambient temperature around the suction nozzle 202 within a certain temperature range.

The reaction auxiliary liquid supply system 251 includes reaction auxiliary liquid bottles 215 and 216 and a reaction auxiliary liquid transfer syringe 228. Discharge channels of the reaction auxiliary liquid bottles 215 and 216 merge with a reaction auxiliary liquid channel 271, extend through the liquid temperature control unit 209, and connect to the reservoir unit 250. The reaction auxiliary liquid transfer syringe 228 is connected to the reaction auxiliary liquid channel 271 via a connection channel 273. A solenoid valve 226 is arranged between the connection position of the connection channel 273 in the reaction auxiliary liquid channel 271 and the liquid temperature control unit 209. The solenoid valve 226 opens and closes the channel according to commands from the controller 119. A liquid waste channel 275, which is connected to the reaction auxiliary liquid channel 271, is also provided with a solenoid valve 224 for opening and closing the channel according to commands from the controller 119. A supply channel 230 for injecting system water (water for syringe channels) is connected to a tube part of the reaction auxiliary liquid transfer syringe 228. A solenoid valve 232 arranged between the reaction auxiliary liquid transfer syringe 228 and the supply channel 230 opens and closes the channel according to commands from the controller 119. The system water is constantly supplied by a liquid transfer mechanism (e.g., pump) during the operation of the analyzer. The system water is used when the reaction auxiliary liquid channel 271 or the connection channel 273 needs the supply of the system water or for diluting the reaction auxiliary liquid. The number of the reaction auxiliary liquid bottles can also be one, or three or more. By employing two or more reaction auxiliary liquid bottles, the operation can be continued by switching the bottle even when one bottle becomes empty.

The discharge channels of the reaction auxiliary liquid bottles 215 and 216 are respectively provided with solenoid valves 220 and 221 for opening and closing the channel. A liquid interruption sensor 219 is arranged between the reaction auxiliary liquid bottle 215/216 and the solenoid valve 220/221. The liquid interruption sensor 219 is a sensor for detecting whether or not the reaction auxiliary liquid is properly drawn out from the reaction auxiliary liquid bottle 215/216 when the supply of the reaction auxiliary liquid is commanded. When the liquid interruption is detected by the sensor, the controller 119 issues an alarm and interrupts the analysis. The reaction auxiliary liquid bottles 215 and 216 are replaced by an operator of the analyzer. The liquid interruption sensor 219 is used in each channel since a difference occurs between a management value used by the controller 119 and the actual amount of the solution in cases where the remaining amount of the bottle after the replacement differs from the amount recognized by the controller 119. An optical sensor for optically detecting the presence/absence of the liquid in the discharge channel, a pressure sensor for detecting pressure variations in the discharge channel at times of suction and liquid transfer, etc. are usable as the liquid interruption sensor 219.

The cleaning liquid supply system 252 is configured similarly to the reaction auxiliary liquid supply system 251. Specifically, the cleaning liquid supply system 252 includes cleaning liquid bottle 217 and 218 and a cleaning liquid transfer syringe 229. Discharge channels of the cleaning liquid bottles 217 and 218 merge with a cleaning liquid channel 272, extend through the liquid temperature control unit 209, and connect to the reservoir unit 250. The cleaning liquid transfer syringe 229 is connected to the cleaning liquid channel 272 via a connection channel 274. A solenoid valve 227 is arranged between the connection position of the connection channel 274 in the cleaning liquid channel 272 and the liquid temperature control unit 209. The solenoid valve 227 opens and closes the channel according to commands from the controller 119. A liquid waste channel 276, which is connected to the cleaning liquid channel 272, is also provided with a solenoid valve 225 for opening and closing the channel according to commands from the controller 119. The supply channel 230 for injecting the system water (water for syringe channels) is connected to a tube part of the cleaning liquid transfer syringe 229. A solenoid valve 234 arranged between the cleaning liquid transfer syringe 229 and the supply channel 230 opens and closes the channel according to commands from the controller 119. The system water is constantly supplied by the liquid transfer mechanism (e.g., pump) during the operation of the analyzer. The system water is used when the cleaning liquid channel 272 or the connection channel 274 needs the supply of the system water or for diluting the cleaning liquid. The number of the cleaning liquid bottles can also be one, or three or more. By employing two or more cleaning liquid bottles, the operation can be continued by switching the bottle even when one bottle becomes empty.

The discharge channels of the cleaning liquid bottles 217 and 218 are respectively provided with solenoid valve 222 and 223 for opening and closing the channel. A liquid interruption sensor 219 is arranged between the cleaning liquid bottle 217/218 and the solenoid valve 222/223. The liquid interruption sensor 219 is a sensor for detecting whether or not the cleaning liquid is properly drawn out from the cleaning liquid bottle 217/218 when the supply of the cleaning liquid is commanded. When the liquid interruption is detected by the sensor, the controller 119 issues an alarm and interrupts the analysis. The purpose of the installation of the liquid interruption sensor 219 in the cleaning liquid supply system 252 is equivalent to that of the liquid interruption sensor 219 in the reaction auxiliary liquid supply system 251, and thus the same types of sensors are usable.

The cleaning liquid supply system 235 for the cleaning of the overflow part includes a cleaning liquid bottle 236, a cleaning liquid transfer syringe 237, and a solenoid valve 238 arranged in a discharge channel of the cleaning liquid transfer syringe 237. A discharge channel of the cleaning liquid bottle 236 merges with the discharge channel of the cleaning liquid transfer syringe 237, extends through the liquid temperature control unit 209, and connects to the reservoir unit 250. The solenoid valve 238 opens and closes the channel according to commands from the controller 119. The supply channel 230 for injecting the system water (water for syringe channels) is connected to a tube part of the cleaning liquid transfer syringe 237. One cleaning liquid bottle 236 or two or more cleaning liquid bottles 236 may be used. The cleaning liquid bottle 236 may also be configured to detect the liquid interruption by use of a liquid interruption sensor 219 like the reaction auxiliary liquid bottles 215 and 216.

The reservoir unit 250 includes a vessel holding member 207 arranged under the suction nozzle 202, a holding member drive mechanism 206 for rotating and vertically moving the vessel holding member 207, a liquid channel 211 for the transfer of liquid supplied to each type of liquid vessel held by the vessel holding member 207, and a tank 253 for receiving liquid discharged from each type of liquid vessel held by the vessel holding member 207. The vessel holding member 207 holds liquid vessels of reaction solution, reaction auxiliary liquid, cleaning liquid, etc. (explained later). According to the detecting operation, the holding member drive mechanism 206 rotates the vessel holding member 207 and properly moves each vessel to a position right under the suction nozzle 202, while also inserting/pulling out the suction nozzle 202 into/from the liquid vessel by vertically moving the vessel holding member 207. A waste channel 214 is connected to the tank 253. Liquid waste that has been lead to the tank 253 is discharged through the waste channel 214.

Figure 3:
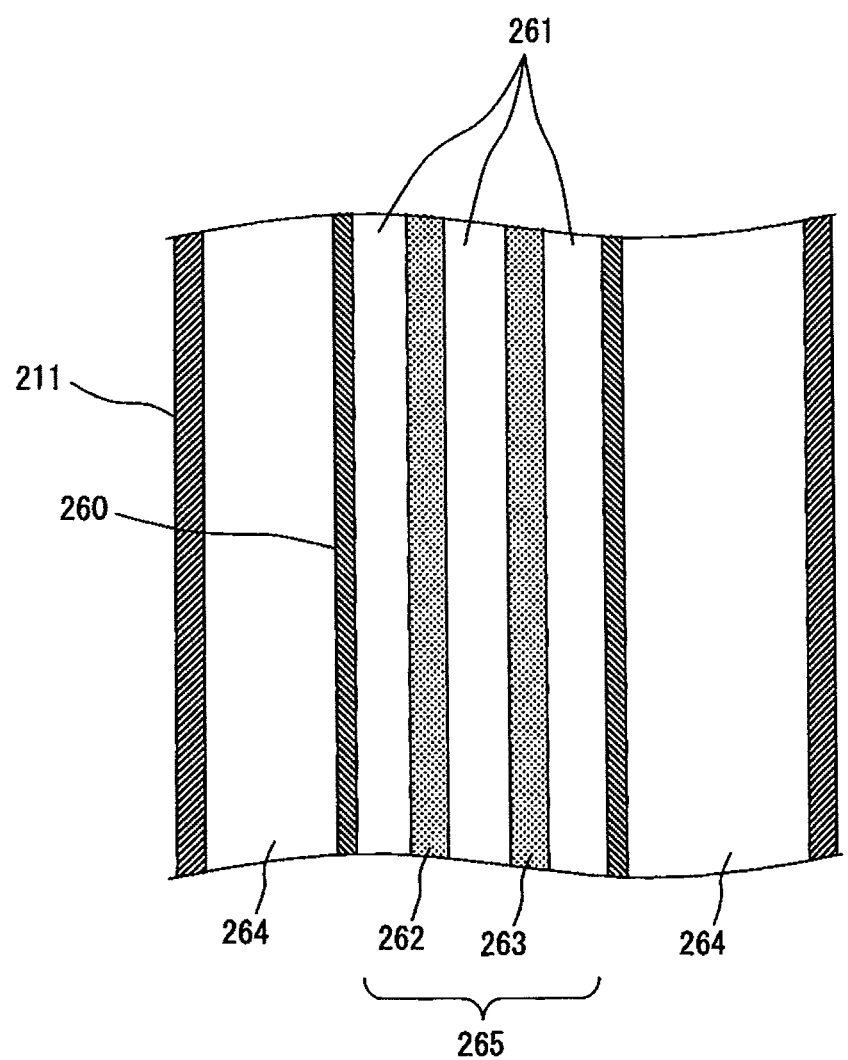
FIG. 3 is an enlarged view of a part III in FIG. 2 (vertical sectional view of a liquid channel).

FIG. 3 is an enlarged view of the part III in FIG. 2 (vertical sectional view of the liquid channel 211).

As shown in FIG. 3, the liquid channel 211 has a double-pipe structure including internal piping 260. The liquid channel 211 includes a supply channel 265 (inside the internal piping 260) and a drain channel 264. The drain channel 264 connects to the tank 253. Reaction auxiliary liquid piping 262 and cleaning liquid piping 263 are arranged in the internal piping 260. The reaction auxiliary liquid piping 262 connects to the reaction auxiliary liquid channel 271 of the aforementioned reaction auxiliary liquid supply system 251. The cleaning liquid piping 263 connects to the cleaning liquid channel 272 of the cleaning liquid supply system 252. The cleaning liquid supply system 235 for the cleaning of the overflow part connects to a hollow part 261 of the internal piping 260 (a channel inside the internal piping 260 and outside the reaction auxiliary liquid piping 262 and the cleaning liquid piping 263). The cleaning liquid (cleaning water in this example) for the cleaning of the overflow part 502 (explained later) flows through the hollow part 261. This cleaning liquid is also adjusted within a prescribed temperature range by the liquid temperature control unit 209 similarly to the liquids flowing through the reaction auxiliary liquid piping 262 and the cleaning liquid piping 263. The cleaning liquid in the hollow part 261 serves also for maintaining the temperature of the reaction auxiliary liquid and the cleaning liquid in the internal piping 260. Incidentally, the drain channel 264 and the supply channel 265 are thermally insulated from each other by use of a heat insulator, by which the thermal influence of the drain channel 264 is suppressed and temperature variations of the supply channel 265 are reduced.

Figure 4:
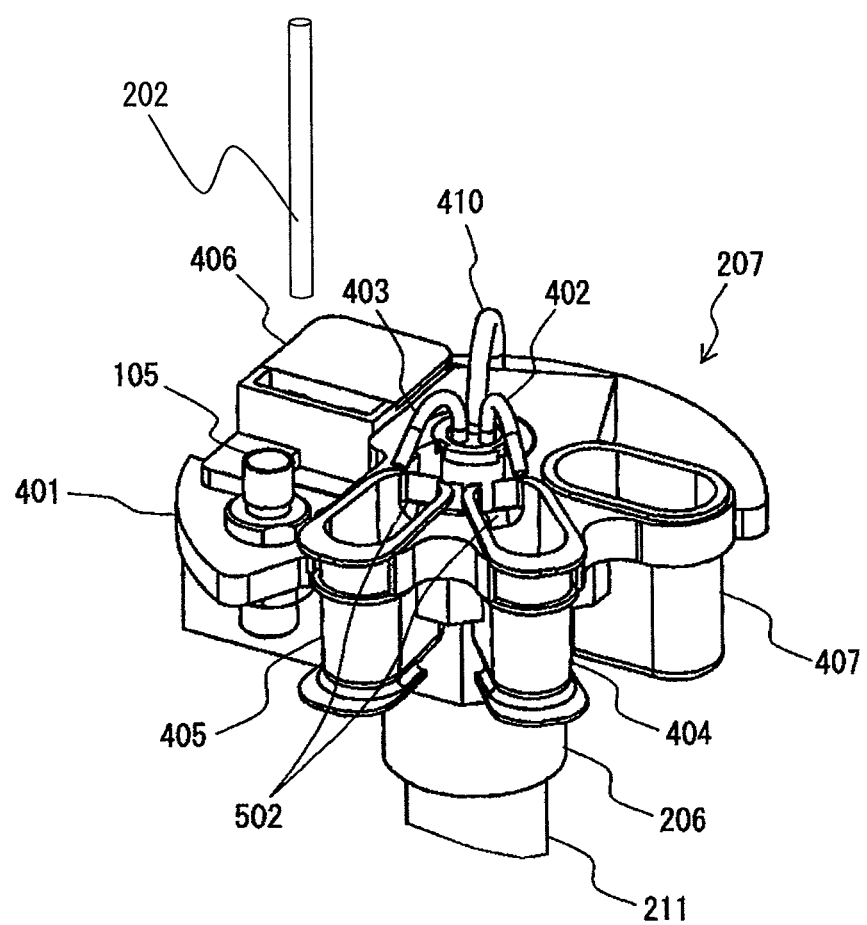
FIG. 4 is a perspective view of a vessel holding member of the automatic analyzer in accordance with a first embodiment of the present invention.

FIG. 4 is a perspective view of the vessel holding member 207.

The vessel holding member 207 includes a reaction auxiliary liquid supply nozzle 402 which is connected to the reaction auxiliary liquid piping 262, a cleaning liquid supply nozzle 403 which is connected to the cleaning liquid piping 263, piping 410 which is connected to the hollow part 261, a reaction vessel setting part 401 in which the reaction vessel 105 is set, a cleaning tank 406 for the cleaning of the suction nozzle 202, a reaction auxiliary liquid vessel 404 storing the reaction auxiliary liquid, a cleaning liquid vessel 405 storing the cleaning liquid, and a special cleaning liquid vessel 407.

The reaction vessel setting part 401, the cleaning tank 406, the reaction auxiliary liquid vessel 404, the cleaning liquid vessel 405 and the special cleaning liquid vessel 407 are arranged around the liquid channel 211 in a circular pattern. The reaction auxiliary liquid vessel 404 and the cleaning liquid vessel 405 are detachable. The reaction auxiliary liquid supply nozzle 402 is connected to the reaction auxiliary liquid piping 262. The cleaning liquid supply nozzle 403 and the piping 410 are connected to the cleaning liquid piping 263. The reaction auxiliary liquid supply nozzle 402 and the cleaning liquid supply nozzle 403 extend upward from their connection parts with the liquid channel 211 and thereafter bend downward with their tip ends facing the reaction auxiliary liquid vessel 404 and the cleaning liquid vessel 405, respectively. The piping 410 is connected to the cleaning tank 406. The reaction auxiliary liquid supply nozzle 402, the cleaning liquid supply nozzle 403 and the piping 410 are held by the vessel holding member 207 or the holding member drive mechanism 206, and thus their positional relationship with the reaction auxiliary liquid vessel 404, the cleaning liquid vessel 405 and the cleaning tank 406 does not change even when the vessel holding member 207 is rotated by the holding member drive mechanism 206. The special cleaning liquid vessel 407 stores a special cleaning liquid which is used for cleaning the flow cell 201, etc. at times of maintenance or the like.

Figure 5:
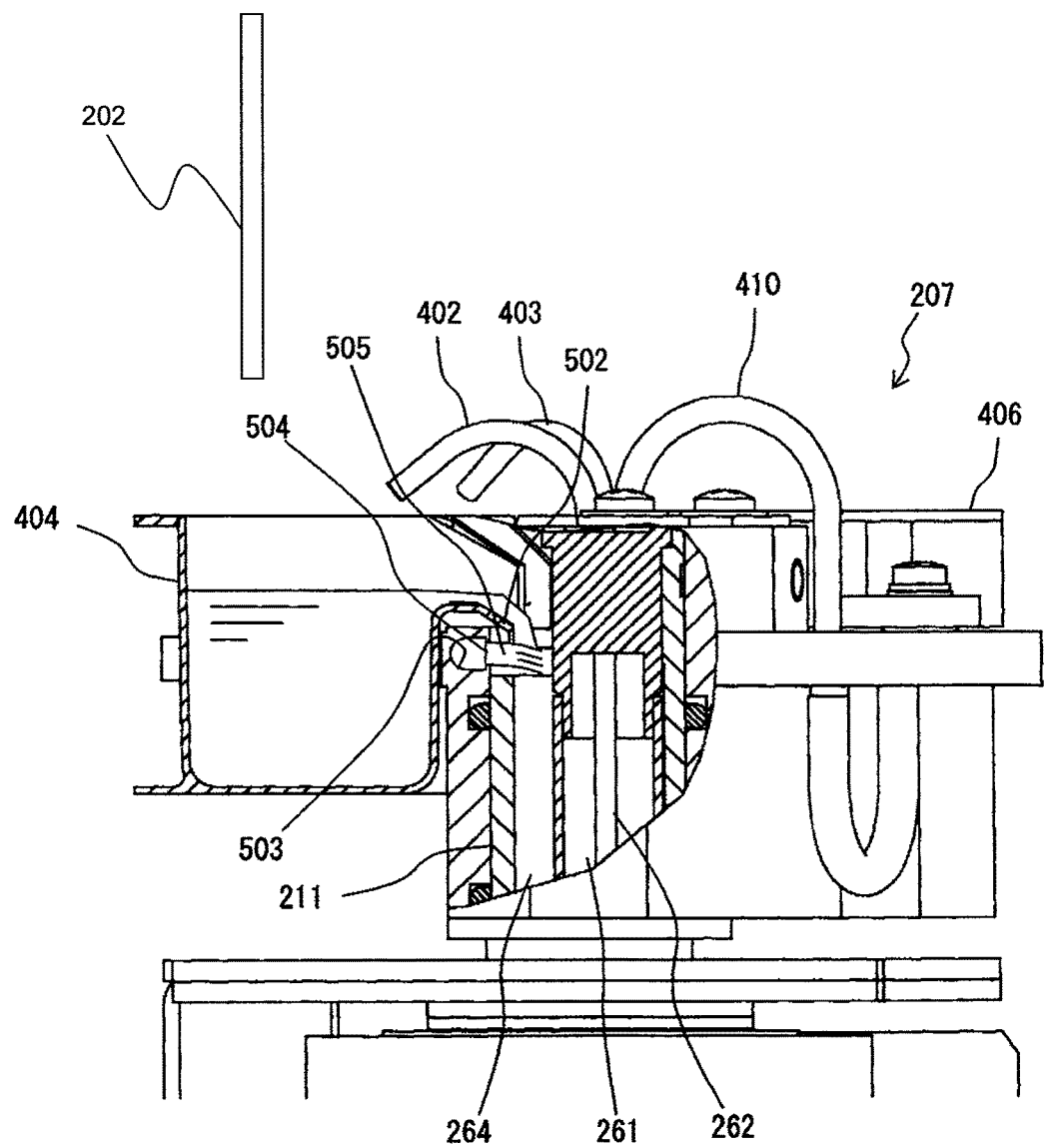
FIG. 5 is a schematic diagram showing the configuration of the vessel holding member of the automatic analyzer in accordance with a first embodiment of the present invention (partially cutaway side view of the vessel holding member showing cross sections of a reaction auxiliary liquid vessel and its surroundings.

FIG. 5 is a partially cutaway side view of the vessel holding member 207 showing cross sections of the reaction auxiliary liquid vessel 404 and its surroundings. While the configuration of the reaction auxiliary liquid vessel 404 and its surroundings is illustrated in FIG. 5, the cleaning liquid vessel 405 and its surroundings are also configured in the same way, and thus repeated explanation thereof is omitted for brevity.

The reaction auxiliary liquid vessel 404 has the overflow part 502. The overflow part 502 is a part used for making the remaining reaction auxiliary liquid overflow into the drain channel 264 (as a dumping part) together with a diluting fluid by supplying the diluting fluid from the reaction auxiliary liquid supply nozzle 402. The overflow part 502 is formed in a shape like a gutter at a position lower than the upper edge of the reaction auxiliary liquid vessel 404 and on the drain channel 264's side of the reaction auxiliary liquid vessel 404. The maximum water level of the reaction auxiliary liquid vessel 404 is determined by the position of the overflow part 502. Liquid hardly accumulates in the overflow part 502 thanks to the gutter-like shape of the overflow part 502.

A cleaning liquid supply channel 503 is formed at a position under the overflow part 502 and within the thickness of a wall between the reaction auxiliary liquid vessel 404 and the liquid channel 211. In this embodiment, the cleaning liquid supply channel 503 is connected to the cleaning liquid supply system 235 (for the cleaning of the overflow part) via the aforementioned hollow part 261. A cleaning liquid discharge outlet 504 as the discharging end of the cleaning liquid supply channel 503 is situated just under the overflow part 502, and thus the cleaning liquid 505 discharged from the cleaning liquid discharge outlet 504 interferes with the tip end part of the overflow part 502 and then flows out into the drain channel 264. The cleaning liquid discharge outlet 504 is also arranged at an equivalent position of the cleaning liquid vessel 405.

Incidentally, the vessel holding member 207 is stored in a semi-enclosed space partitioned by the lower surface of the detection unit 116, a cover 208, etc. as shown in FIG. 2. The air temperature control unit 212 sends temperature-controlled air to the inside of the space through a circulating air outlet 213 and thereby keeps the vicinity of the vessel holding member 207 within a prescribed temperature range. The liquid temperature control unit 209 is situated between the reaction auxiliary liquid supply system 251 and the reservoir unit 250 and between the cleaning liquid supply system 252 and the reservoir unit 250 and adjusts the reaction auxiliary liquid and the cleaning liquid (supplied from the reaction auxiliary liquid supply system 251 and the cleaning liquid supply system 252 to the reservoir unit 250) within a certain temperature range.

(2) Detecting Operation

Figure 6:
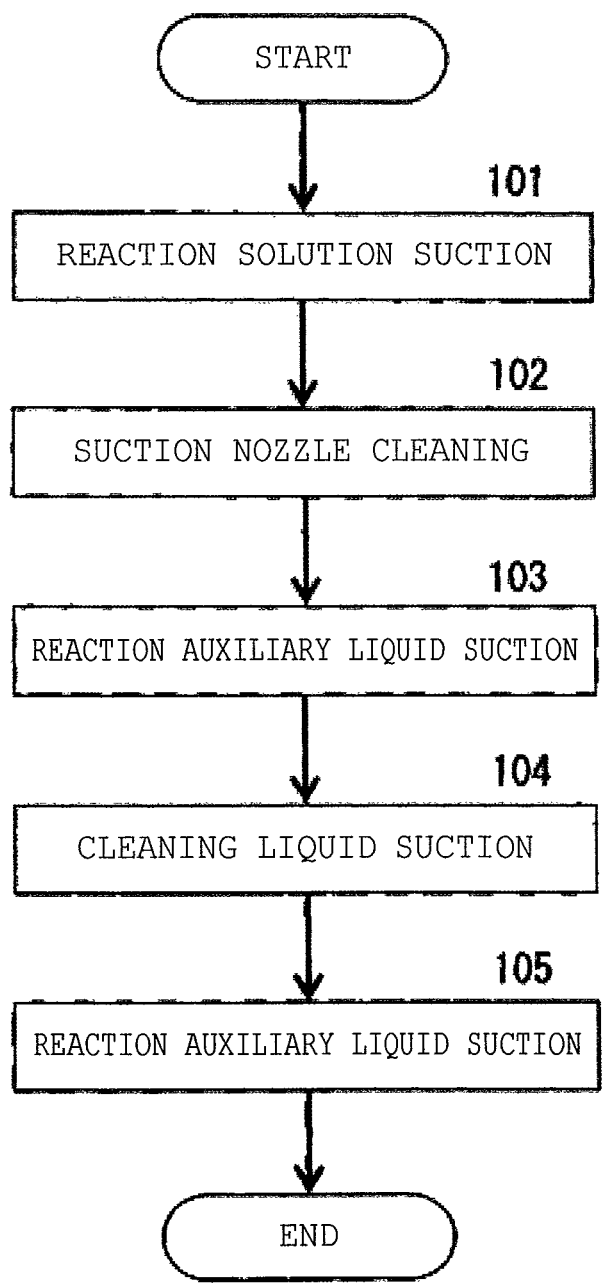
FIG. 6 is a flow chart showing a control procedure performed by a controller for the detection of particular substances contained in a reaction solution.

FIG. 6 is a flow chart showing a control procedure performed by the controller 119 for the detection of particular substances contained in a reaction solution.

(Step 101)

Step 101 is a step of sucking in a reaction solution and transferring the reaction solution to the flow cell 201. In this step, the controller 119 first commands the incubator disk 104, the reaction vessel transfer mechanism 115 and the holding member drive mechanism 206 to move a prescribed reaction vessel 105 on the incubator disk 104 to the reaction vessel setting part 401 of the vessel holding member 207, rotate the vessel holding member 207, and thereby move the reaction vessel 105 to the position right under the suction nozzle 202. Then, the suction nozzle 202 is inserted into the reaction vessel 105 by elevating the vessel holding member 207. The suction nozzle 202 is inserted to the bottom of the reaction vessel 105 at this point. In this case, the suction nozzle 202 is kept in contact with the bottom of the reaction vessel 105 with a prescribed pressure since the reaction vessel setting part 401 is configured to be elastically movable downward with respect to the vessel holding member 207.

After inserting the suction nozzle 202 into the reaction vessel 105, the controller 119 opens the flow cell 201's side of the channel selector valve 204 arranged in the suction channel 205 and closes the waste channel 205a's side of the channel selector valve 204 while keeping the suction nozzle 202 inserted in the reaction vessel 105. Then, the controller 119 drives the liquid transfer syringe 203 in the sucking direction (downward) and thereby transfers the reaction solution to the inside of the flow cell 201 via the suction nozzle 202. At this point, a magnet (unshown) for capturing magnetic particles is brought to a position immediately under the flow cell 201, by which a magnetic particle composite, including the objects of analysis and detection labels in the reaction solution flowing through the flow cell 201, is magnetically captured inside the flow cell 201.

(Step 102)

Step 102 is a step of cleaning the suction nozzle 202 and thereby removing the reaction solution adhering to the suction nozzle 202. After finishing the suction of the reaction solution by the suction nozzle 202, the controller 119 advances to this step and commands the holding member drive mechanism 206 to lower the vessel holding member 207 and thereby pull out the suction nozzle 202 from the reaction vessel 105. Subsequently, the cleaning tank 406 is moved to the position right under the suction nozzle 202 by rotating the vessel holding member 207 and then the suction nozzle 202 is inserted into the cleaning tank 406 by elevating the vessel holding member 207. In the cleaning tank 406, the cleaning liquid supplied through a cleaning liquid supply hole (unshown) flies toward the peripheral part of the suction nozzle 202 and flows out to the drain channel 264 while removing the reaction solution adhering to the peripheral part of the suction nozzle 202.

(Step 103)

Step 103 is a step of having the suction nozzle 202 suck in the reaction auxiliary liquid and thereby transferring the reaction auxiliary liquid to the flow cell 201. After finishing the cleaning of the suction nozzle 202, the controller 119 advances to this step and commands the holding member drive mechanism 206 to lower the vessel holding member 207 and thereby pull out the suction nozzle 202 from the cleaning tank 406. Subsequently, the reaction auxiliary liquid vessel 404 is moved to the position right under the suction nozzle 202 by rotating the vessel holding member 207 and then the suction nozzle 202 is inserted into the reaction auxiliary liquid vessel 404 by elevating the vessel holding member 207. Incidentally, the vessel holding member 207 is configured so that the reaction vessel setting part 401 is situated at the holding position (grabbing position) of the reaction vessel transfer mechanism 115 when the reaction auxiliary liquid vessel 404 is at the position right under the suction nozzle 202. When the reaction auxiliary liquid vessel 404 is moved to the position right under the suction nozzle 202, the controller 119 commands the reaction vessel transfer mechanism 115 to take hold of the reaction vessel 105 and transfer the reaction vessel 105 from the reaction vessel setting part 401 to a waste reaction vessel setting part on the incubator disk 104. With this configuration of the vessel holding member 207 allowing the reaction vessel transfer mechanism 115 to access the reaction vessel setting part 401 while the suction nozzle 202 is accessing the reaction auxiliary liquid vessel 404, the analysis time can be shortened.

Thereafter, the reaction auxiliary liquid is sucked in through the suction nozzle 202 and the reaction solution remaining in the flow cell 201 is replaced with the reaction auxiliary liquid while maintaining the state in which the magnetic particle composite is magnetically captured inside the flow cell 201. After finishing the suction of the reaction auxiliary liquid, the controller 119 separates the magnet (unshown) for capturing magnetic particles from the flow cell 201 and then commands the detector 200 to determine the quantity of each measurement object by detecting the detection labels contained in the magnetic particle composite in the flow cell 201. The result of the measurement is sent to the controller 119.

Incidentally, the controller 119 commands the reaction auxiliary liquid supply system 251 to charge the reaction auxiliary liquid vessel 404 with the same amount of reaction auxiliary liquid (as the reaction auxiliary liquid sucked in by the suction this time) through the reaction auxiliary liquid supply nozzle 402 before the next suction of the reaction auxiliary liquid (e.g., simultaneously with or just after the suction by the suction nozzle 202). With this operation, the amount of the liquid in the reaction auxiliary liquid vessel 404 is maintained at a minimum and fixed volume. This prevents the overflow and bubbling of the liquid in each vessel during the transfer and stabilizes the rotation and the vertical movement of the vessel holding member 207. Consequently, improvement in analysis cycle efficiency and analysis performance is expected.

(Step 104)

Step 104 is a step of sucking in the cleaning liquid through the suction nozzle 202 and thereby cleaning the flow cell 201. After finishing the detecting operation and advancing to this step, the controller 119 commands the holding member drive mechanism 206 to lower the vessel holding member 207 and thereby pull out the suction nozzle 202 from the reaction auxiliary liquid vessel 404. Subsequently, the cleaning liquid vessel 405 is moved to the position right under the suction nozzle 202 by rotating the vessel holding member 207 and then the suction nozzle 202 is inserted into the cleaning liquid vessel 405 by elevating the vessel holding member 207. Thereafter, the magnetic particles and the reaction auxiliary liquid remaining in the flow cell 201 are cleaned off by having the suction nozzle 202 suck in the cleaning liquid in the same way as the aforementioned operation. Similarly to the charging with the reaction auxiliary liquid, the same amount of cleaning liquid (as the volume sucked in by the suction nozzle 202) is supplied to the cleaning liquid vessel 405 through the cleaning liquid supply nozzle 403 before the next suction of the cleaning liquid (e.g., simultaneously with or just after the suction by the suction nozzle 202). This stabilizes the rotation and the vertical movement of the vessel holding member 207, achieving the improvement in the analysis cycle efficiency and the analysis performance.

(Step 105)

Step 105 is a step for the preparation for the next detecting operation. After finishing the suction of the cleaning liquid and advancing to this step, the controller 119 commands the holding member drive mechanism 206 to lower the vessel holding member 207 and thereby pull out the suction nozzle 202 from the cleaning liquid vessel 405. Subsequently, the reaction auxiliary liquid vessel 404 is moved to the position right under the suction nozzle 202 by rotating the vessel holding member 207 and then the suction nozzle 202 is inserted into the reaction auxiliary liquid vessel 404 by elevating the vessel holding member 207. Then, the reaction auxiliary liquid is sucked in through the suction nozzle 202 and the cleaning liquid remaining in the flow cell 201 is replaced with the reaction auxiliary liquid. In the period in which the reaction auxiliary liquid vessel 404 is at the position right under the suction nozzle 202, the controller 119 commands the reaction vessel transfer mechanism 115 to transfer a prescribed reaction vessel 105 from the incubator disk 104 to the reaction vessel setting part 401 and performs a preparation process for the next detecting operation. Also in this step, the controller 119 charges the reaction auxiliary liquid vessel 404 with the reaction auxiliary liquid before the next suction of the reaction auxiliary liquid.

The automatic analyzer of this embodiment carries out a plurality of analyses efficiently by repeating the analysis procedure (steps 101-105) explained above.

Incidentally, the automatic analyzer of this embodiment has two reaction auxiliary liquid bottles and two cleaning liquid bottles so that each of the bottles used can be replaced. For example, if the empty state of the first reaction auxiliary liquid bottle 215 is detected by the liquid interruption sensor 219 (arranged in the pipeline of the reaction auxiliary liquid bottle 215) when the first reaction auxiliary liquid bottle 215 is in use with the solenoid valves 221, 224 and 232 closed and the solenoid valves 220 and 226 open, the controller 119 switches the used bottle to the second reaction auxiliary liquid bottle 216 by closing the solenoid valve 220 and opening the solenoid valve 221. A similar operation is performed also for the cleaning liquid. If the empty state of the first cleaning liquid bottle 217 is detected by the liquid interruption sensor 219 (arranged in the pipeline of the cleaning liquid bottle 217) when the first cleaning liquid bottle 217 is in use with the solenoid valves 223, 225 and 234 closed and the solenoid valves 222 and 227 open, the controller 119 switches the used bottle to the second cleaning liquid bottle 218 by closing the solenoid valve 222 and opening the solenoid valve 223.

(3) Liquid Replacement Operation

Next, an operation for replacing the liquids in the reaction auxiliary liquid vessel 404, the cleaning liquid vessel 405, the reaction auxiliary liquid channel 271, the cleaning liquid channel 272, etc. along with the replacement of the reaction auxiliary liquid will be explained below. The following operation is applicable also to cases where the liquids in the cleaning liquid vessel 405, the cleaning liquid channel 272, etc. are replaced.

Figure 7:
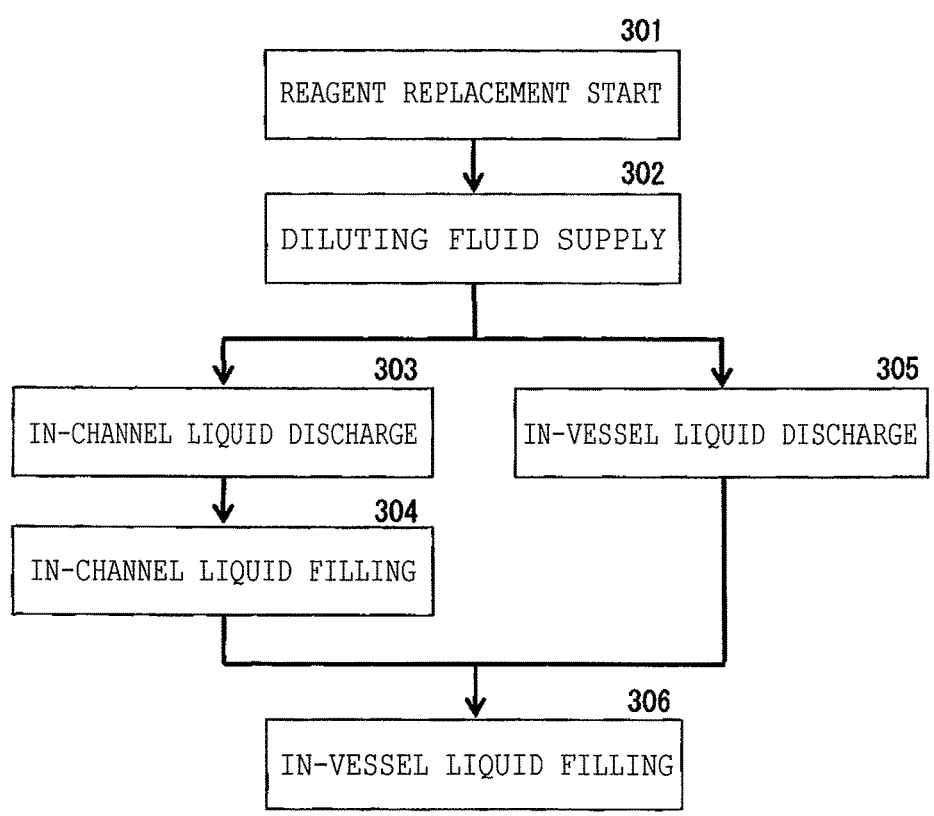
FIG. 7 is a flow chart showing a control procedure performed by the controller for replacing liquids in liquid vessels and liquid channels.

FIG. 7 is a flow chart showing a control procedure performed by the controller 119 for replacing liquids in liquid vessels and liquid channels.

(Step 301)

When replacement of liquids in liquid vessels and channels is commanded by the operator through an operation unit (unshown) of the controller 119, the controller 119 executes a reagent replacement start process 301 so as to dilute the liquids in the reaction auxiliary liquid vessel 404 and the cleaning liquid vessel 405. Thereafter, the controller 119 advances to a diluting fluid supply process 302.

(Step 302)

In the diluting fluid supply process 302, the controller 119 commands the reaction auxiliary liquid supply system 251 and the cleaning liquid supply system 252 to supply the diluting fluid to the reaction auxiliary liquid vessel 404 and the cleaning liquid vessel 405. Specifically, this step is executed as follows:

First, in the reaction auxiliary liquid supply system 251, the system water as the diluting fluid is drawn from the supply channel 230 into the liquid transfer syringe 228 by having the liquid transfer syringe 228 perform the sucking operation with the solenoid valves 220, 221 and 226 closed and the solenoid valves 224 and 232 open. Thereafter, the diluting fluid is supplied to the reaction auxiliary liquid vessel 404 via the reaction auxiliary liquid channel 271 and the reaction auxiliary liquid supply nozzle 402 by having the liquid transfer syringe 228 perform the discharging operation with the solenoid valves 220, 221 and 224 closed and the solenoid valves 226 and 232 open. This operation is repeated until a prescribed volume of the diluting fluid is supplied (or repeated for a prescribed number of times), by which the liquid (old reaction auxiliary liquid) remaining in the reaction auxiliary liquid vessel 404 is diluted to a prescribed dilution rate or thinner.

Meanwhile, the controller 119 also commands the cleaning liquid supply system 252 to perform a similar operation. Specifically, in the cleaning liquid supply system 252, the system water as the diluting fluid is drawn from the supply channel 230 into the liquid transfer syringe 229 by having the liquid transfer syringe 229 perform the sucking operation with the solenoid valves 222, 223 and 227 closed and the solenoid valves 225 and 234 open. Thereafter, the diluting fluid is supplied to the cleaning liquid vessel 405 via the cleaning liquid channel 272 and the cleaning liquid supply nozzle 403 by having the liquid transfer syringe 229 perform the discharging operation with the solenoid valves 222, 223 and 225 closed and the solenoid valves 227 and 234 open. This operation is repeated until a prescribed volume of the diluting fluid is supplied (or repeated for a prescribed number of times), by which the liquid (old cleaning liquid) remaining in the cleaning liquid vessel 405 is diluted to a prescribed dilution rate or thinner.

By the above operations, old reaction auxiliary liquid and old cleaning liquid remaining in the reaction auxiliary liquid channel 271 and the cleaning liquid channel 272 are pushed out by the diluting fluid to the reaction auxiliary liquid vessel 404 and the cleaning liquid vessel 405, respectively. Since a large amount of diluting fluid exceeding the capacities of the reaction auxiliary liquid vessel 404 and the cleaning liquid vessel 405 is continuously supplied in this step, the reaction auxiliary liquid and the cleaning liquid which have been pushed out and removed are dumped from the overflow part 502 to the drain channel 264 together with the diluting fluid.

After finishing the diluting fluid supply process 302, the controller 119 advances to an in-channel liquid discharge process 303 and an in-vessel liquid discharge process 305.
(Step 303)

In the in-channel liquid discharge process 303, the controller 119 commands the reaction auxiliary liquid supply system 251 and the cleaning liquid supply system 252 to discharge the liquids remaining in the channels such as the reaction auxiliary liquid channel 271 and the cleaning liquid channel 272. Specifically, in the reaction auxiliary liquid supply system 251, the liquid in the channel is sucked into the liquid transfer syringe 228 by having the liquid transfer syringe 228 perform the sucking operation with the solenoid valves 220, 221, 224 and 232 closed and the solenoid valve 226 open, for example. Thereafter, the liquid in the channel is discharged through the liquid waste channel 275 by having the liquid transfer syringe 228 perform the discharging operation with the solenoid valves 226 closed and the solenoid valve 224 open. Meanwhile, in the cleaning liquid supply system 252, the liquid in the channel is sucked into the liquid transfer syringe 229 by having the liquid transfer syringe 229 perform the sucking operation with the solenoid valves 222, 223, 225 and 234 closed and the solenoid valve 227 open, for example. Thereafter, the liquid in the channel is discharged through the liquid waste channel 276 by having the liquid transfer syringe 229 perform the discharging operation with the solenoid valves 227 closed and the solenoid valve 225 open.
(Step 304)

After finishing the in-channel liquid discharge process 303, the controller 119 executes an in-channel liquid filling process 304, in which the controller 119 commands the reaction auxiliary liquid supply system 251 and the cleaning liquid supply system 252 to fill the reaction auxiliary liquid into the channels between the liquid waste channel 275 and the reaction auxiliary liquid bottles 215 and 216 and fill the cleaning liquid into the channels between the liquid waste channel 276 and the cleaning liquid bottles 217 and 218. Specifically, in the reaction auxiliary liquid supply system 251, the discharging operation of the liquid transfer syringe 228 is performed with the solenoid valves 221, 226 and 232 closed and the solenoid valves 220 and 224 open, and the solenoid valve 224 is closed at the point when the liquid waste channel 275 has been filled with the reaction auxiliary liquid, for example. Meanwhile, in the cleaning liquid supply system 252, the discharging operation of the liquid transfer syringe 229 is performed with the solenoid valves 223, 227 and 234 closed and the solenoid valves 222 and 225 open, and the solenoid valve 225 is closed at the point when the liquid waste channel 276 has been filled with the reaction auxiliary liquid, for example.
(Step 305)

Figure 8:
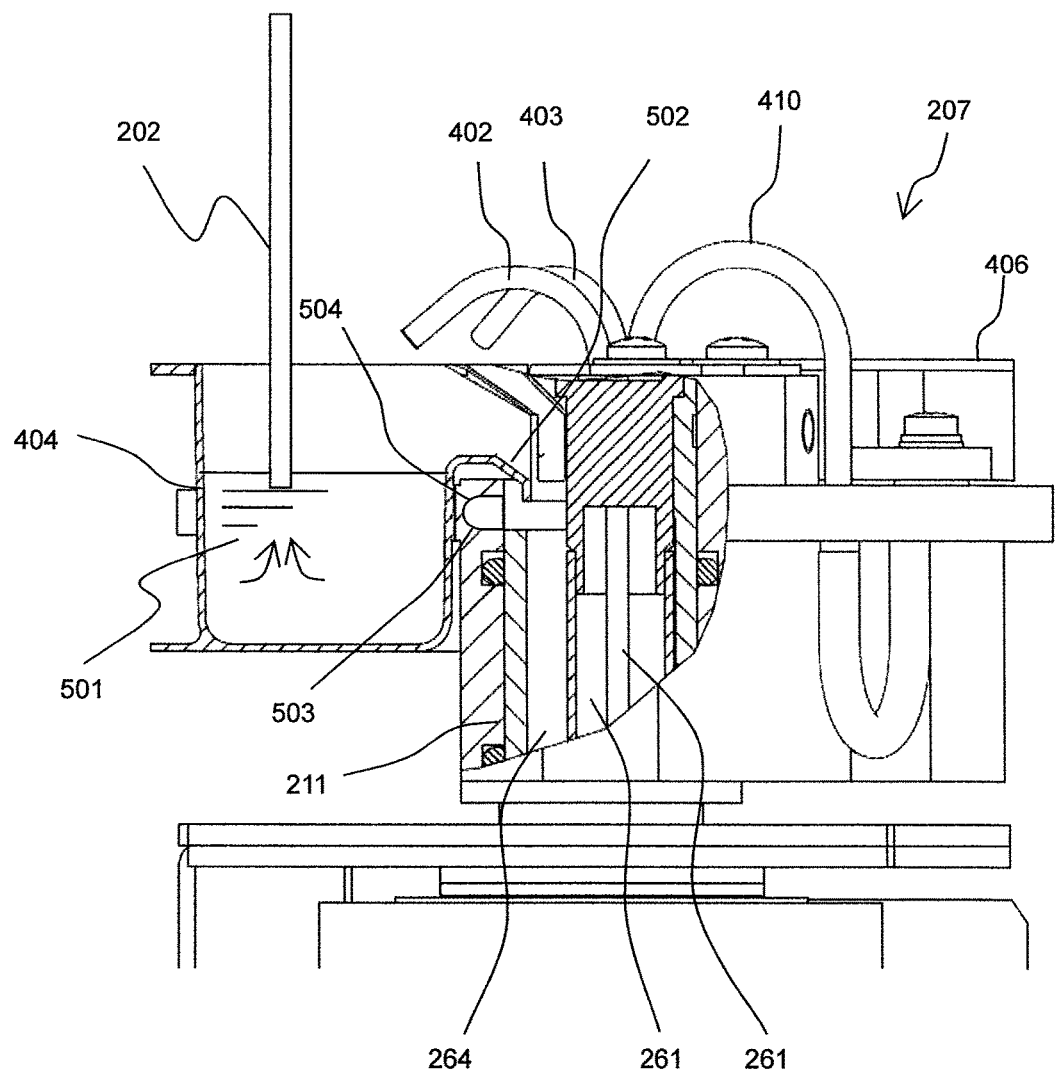
FIG. 8 is a schematic diagram showing the suction of liquid from the reaction auxiliary liquid vessel.
Figure 9:
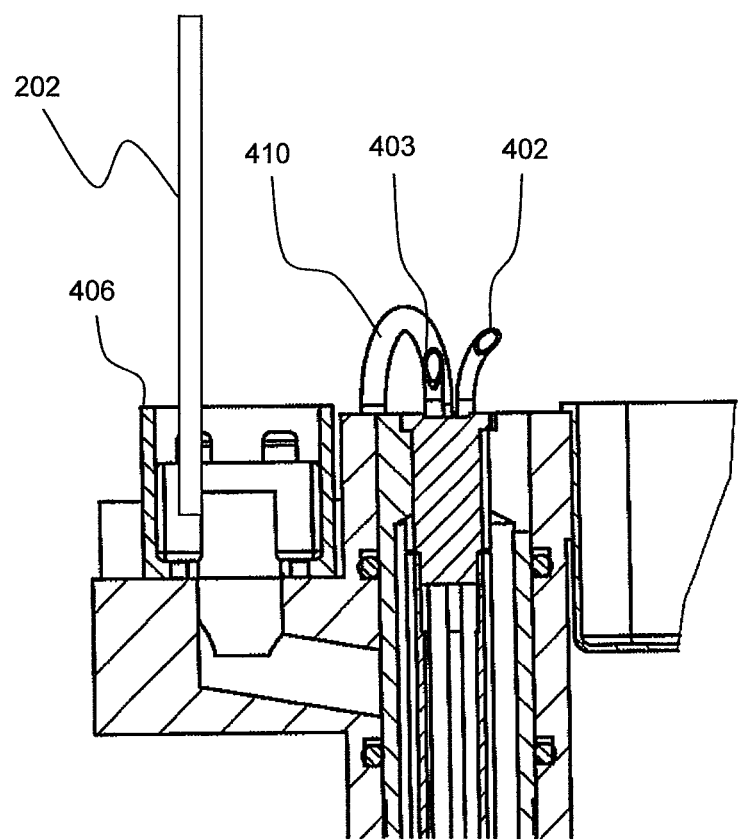
FIG. 9 is a schematic diagram showing the discharging of the sucked liquid into a cleaning tank.

After finishing the aforementioned diluting fluid supply process 302, the controller 119 executes the in-vessel liquid discharge process 305 in parallel with the in-channel liquid discharge process 303. In the in-vessel liquid discharge process 305, the controller 119 commands the channel selector valve 204, the liquid transfer syringe 203 and the holding member drive mechanism 206 to discharge the liquids in the reaction auxiliary liquid vessel 404 and the cleaning liquid vessel 405. Specifically, the controller 119 first commands the holding member drive mechanism 206 to move the reaction auxiliary liquid vessel 404 to the position right under the suction nozzle 202 and elevate the reaction auxiliary liquid vessel 404 to the sucking position. Thereafter, the controller 119 opens the channel selector valve 204 to the suction channel 205's side and commands the liquid transfer syringe 203 to suck in the liquid in the reaction auxiliary liquid vessel 404 (see FIG. 8). After suction of a certain amount of liquid, the holding member drive mechanism 206 is lowered and rotated so as to bring the cleaning tank 406 to the position right under the suction nozzle 202, and the discharging operation of the liquid transfer syringe 203 is performed to discharge the liquid (sucked in from the vessel) to the cleaning tank 406 (see FIG. 9). The liquid discharged to the cleaning tank 406 is dumped through the drain channel 264. The cleaning of the suction nozzle 202 is also carried out. In cases where the liquid in the reaction auxiliary liquid vessel 404 cannot be totally discharged by one sucking operation, a similar operation is repeated. It is also possible to replace the cleaning liquid in the cleaning tank 406 by supplying the cleaning liquid to the tank during or after the liquid discharge.

Subsequently, the controller 119 has the liquid in the cleaning liquid vessel 405 discharged similarly to the operation for the reaction auxiliary liquid vessel 404. Specifically, the controller 119 commands the holding member drive mechanism 206 to move the cleaning liquid vessel 405 to the position right under the suction nozzle 202 and elevate the cleaning liquid vessel 405 to the sucking position. Thereafter, in the state of opening the channel selector valve 204 to the suction channel 205's side, the controller 119 commands the liquid transfer syringe 203 to suck in the liquid in the cleaning liquid vessel 405. After suction of a certain amount of liquid, the holding member drive mechanism 206 is lowered and rotated so as to bring the cleaning tank 406 to the position right under the suction nozzle 202, and the discharging operation of the liquid transfer syringe 203 is performed to discharge the liquid (sucked in from the vessel) to the cleaning tank 406. At this point, the cleaning of the suction nozzle 202 is also carried out. The liquid discharged to the cleaning tank 406 is dumped through the drain channel 264. In cases where the liquid in the cleaning liquid vessel 405 cannot be totally discharged by one sucking operation, a similar operation is repeated. It is also possible to replace the cleaning liquid in the cleaning tank 406 by supplying the cleaning liquid to the tank during or after the liquid discharge. Incidentally, the order of the processes for the reaction auxiliary liquid vessel 404 and the cleaning liquid vessel 405 may also be reversed.
(Step 306)

After finishing both the in-channel liquid filling process 304 and the in-vessel liquid discharge process 305, the controller 119 advances to an in-vessel liquid filling process 306 to fill the reaction auxiliary liquid vessel 404 and the cleaning liquid vessel 405 with the reaction auxiliary liquid and the cleaning liquid, respectively. Specifically, in the reaction auxiliary liquid supply system 251 and the cleaning liquid supply system 252, the reaction auxiliary liquid vessel 404 and the cleaning liquid vessel 405 are filled with the reaction auxiliary liquid and the cleaning liquid via the reaction auxiliary liquid channel 271 and the cleaning liquid channel 272, respectively, by performing the sucking/discharging operations of the liquid transfer syringes 228 and 229 with the solenoid valves 221, 223-225, 232 and 234 closed and the solenoid valves 220, 222, 226 and 227 open.

While these operations for the reaction auxiliary liquid supply system 251 and the cleaning liquid supply system 252 may be performed by shifting the timing between the systems 251 and 252, the processing time can be shortened by performing the operations concurrently. In cases where each liquid supply system (reaction auxiliary liquid supply system 251, cleaning liquid supply system 252) has two or more detection units 116 and two or more reservoir units 250, the liquid filling operation is successively performed on the vessel holding members 207 of the reservoir units 250. After completing the in-vessel liquid filling process 306, the controller 119 ends this flow.

(4) Action and Effect

According to this embodiment, when the remaining liquid in each liquid vessel undergoing the suction by the suction nozzle 202 (reaction auxiliary liquid vessel 404, cleaning liquid vessel 405) is discharged, the diluting fluid is supplied to the liquid vessel and the remaining liquid is diluted. By the dilution of the remaining liquid to such an extent that the influence of the liquid (when entered the flow cell 201) on the precision of analysis is negligible, the inflow of the liquid (sucked in from each liquid vessel) into the flow cell 201 becomes permissible. Accordingly, a larger amount of liquid can be sucked in and discharged to the cleaning tank 406 by one sucking operation, without being restricted by the channel capacity from the suction nozzle 202 to the flow cell 201. Therefore, the number of repetitions of the suction/discharge necessary for finishing the discharging of the liquid from each liquid vessel can be reduced significantly. This makes it possible to quicken the replacement of the liquid in each liquid vessel, shorten the analysis preparation time, and speed up the processing.

Further, in this embodiment, the diluting fluid is not just supplied to each liquid vessel but supplied over the capacity of the liquid vessel so as to actively cause the overflow of the remaining liquid from the liquid vessel, by which the liquid remaining in each liquid vessel can be diluted more efficiently.

Furthermore, in this embodiment, when liquid (reaction auxiliary liquid, cleaning liquid) is excessively supplied to a liquid vessel, the surplus liquid is discharged from the overflow part 502 to the drain channel 264. Especially when the amount of overflowing liquid is small, the liquid tends to accumulate in the overflow part 502. Infiltration of the accumulating liquid into a drive unit, etc. of the holding member drive mechanism 206 can cause failure in the operation of the holding member drive mechanism 206, liquid supply quantity control of liquid vessels, etc. and can deteriorate the analysis cycle efficiency and the precision of analysis. Thus, by arranging the cleaning liquid supply channel 503 and the cleaning liquid discharge outlet 504 and cleaning the discharging end of the overflow part 502 with the cleaning liquid supplied through the cleaning liquid supply channel 503 and the cleaning liquid discharge outlet 504, the adhesion of the remaining liquid to the overflow part 502 can be suppressed and the deterioration in the analysis cycle efficiency and the precision of analysis can be reduced.

In addition, according to this embodiment, at times of suction/discharging of liquid, the suction nozzle 202 does not move and each liquid vessel is moved with respect to the suction nozzle 202 by rotating and vertically moving the vessel holding member 207. Therefore, deformation, expansion and contraction of the channel from the suction nozzle 202 to the flow cell 201 can be avoided differently from imaginary cases where the suction nozzle 202 is moved with respect to the liquid vessel. This makes it possible to reduce factors causing faulty analysis (change in the liquid flow velocity distribution in a channel, change in status of adsorption/desorption of liquid components to/from the inner surface of a channel, etc.) and improve the precision of analysis. In such a mechanism, if no analysis is performed for a certain period, liquids inside the liquid vessels on the vessel holding member 207 and liquids inside channels connecting to the liquid vessels can be deteriorated by temperature, etc. and the use of such liquids for analysis can have bad influence on the analysis performance. By replacing the liquids inside the liquid vessels and the channels with new liquids before the start of analysis as described above, the influence on the precision of analysis can be eliminated.

2. Second Embodiment

Figure 10:
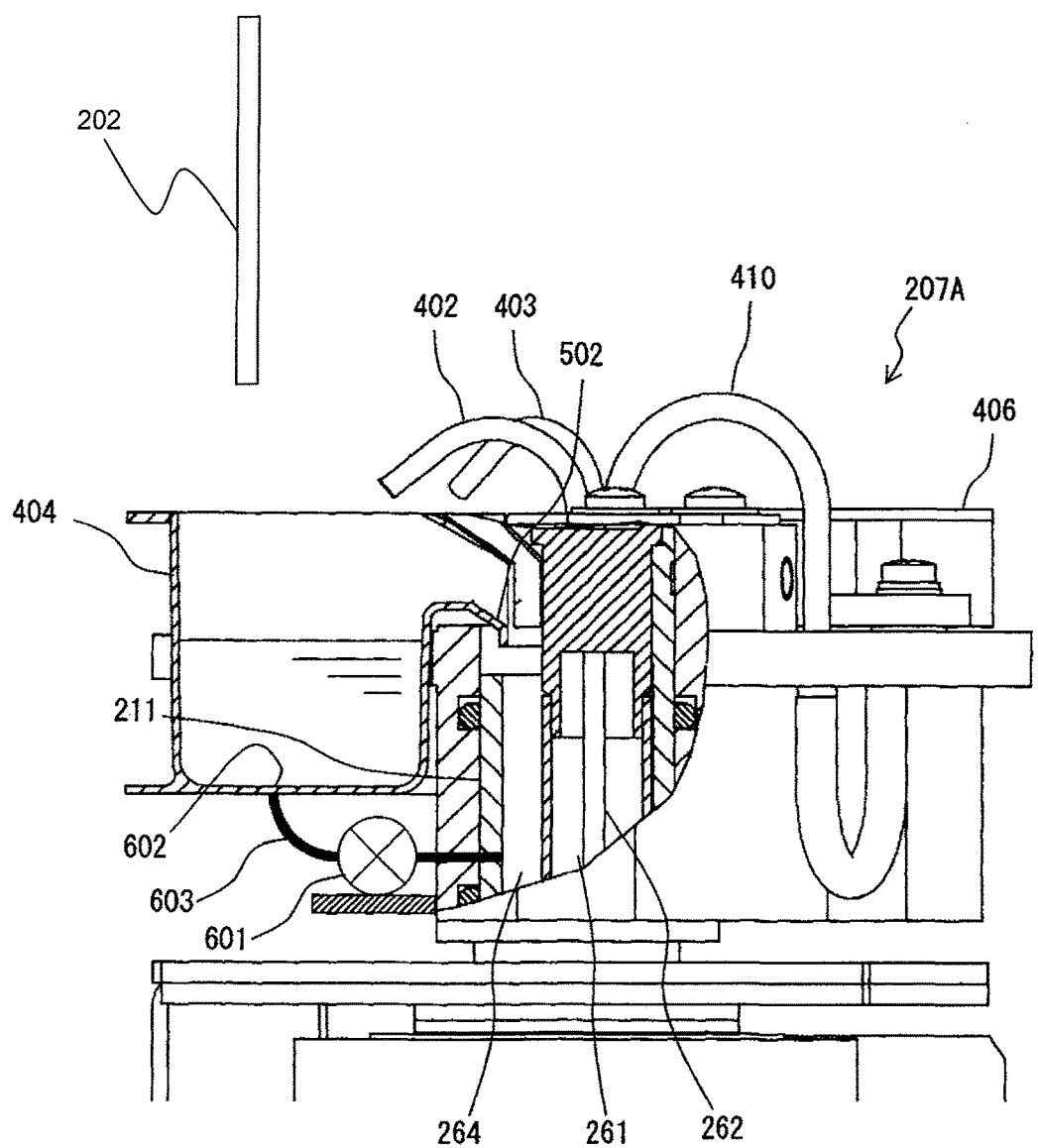
FIG. 10 is a partially cutaway side view of a vessel holding member of an automatic analyzer in accordance with a second embodiment of the present invention.

FIG. 10 is a partially cutaway side view (corresponding to FIG. 5) of a vessel holding member of an automatic analyzer in accordance with a second embodiment of the present invention.

This embodiment differs from the first embodiment in that the liquid vessels (the reaction auxiliary liquid vessel 404, the cleaning liquid vessel 405, etc.) are provided with liquid waste systems. Specifically, a vessel holding member 207A in this embodiment includes a discharge outlet 602 formed at the bottom of each liquid vessel (reaction auxiliary liquid vessel 404, cleaning liquid vessel 405, etc.), a discharge channel 603 connecting the discharge outlet 602 to the drain channel 264 (dumping part), and a control valve 601 arranged in the discharge channel 603. In the aforementioned diluting fluid supply process 302, the controller 119 supplies the diluting fluid to the liquid vessel while also opening the control valve 601, having the liquid overflow from the liquid vessel, and having the remaining liquid discharged from the liquid vessel through the discharge outlet 602 together with the diluting fluid.

Incidentally, while no cleaning liquid supply channel 503 or cleaning liquid discharge outlet 504 is shown in FIG. 10, it is of course possible to form an overflow part cleaning mechanism. The other configuration is equivalent to that in the first embodiment, and thus effects equivalent to those of the first embodiment can be achieved. Further, by the discharging of the remaining liquid from the liquid vessel through the discharge outlet 602 together with the diluting fluid while having the liquid overflow from the liquid vessel, the discharging of the remaining liquid and the dilution of the liquid in the liquid vessel can be carried out effectively and that can contribute to the speeding up of the processing.

3. Other Examples

While the above embodiments have been explained by taking an example in which the cleaning liquid discharged from the cleaning liquid supply channel 503 and the cleaning liquid discharge outlet 504 is used for the cleaning of the overflow part 502, it is also possible to employ a configuration for removing the liquid remaining in the overflow part 502 by blowing air onto the overflow part 502 instead of the cleaning liquid.

While the above embodiments have been explained by taking an example of a configuration in which each liquid vessel (reaction auxiliary liquid vessel 404, cleaning liquid vessel 405, etc.) moves with respect to the suction nozzle 202 fixed at a constant position, the relative movement between each liquid vessel and the suction nozzle 202 may also be implemented by employing a configuration for moving the suction nozzle 202. An automatic analyzer having such a configuration is also capable of implementing the essential features of the present invention (diluting the remaining liquid with the diluting fluid and sucking in the liquid up to the flow cell 201 when the liquid in the liquid vessel is discharged) and achieving similar effects.

While the above embodiments have been explained by taking an example in which the remaining liquids in the reaction auxiliary liquid vessel 404 and the cleaning liquid vessel 405 are diluted by using the system water from the system water supply channel 230 and the solenoid valve 232 as the diluting fluid, other configurations may also be employed. For example, it is possible to arrange a reaction auxiliary liquid diluting fluid bottle and a cleaning liquid diluting fluid bottle respectively between the liquid transfer syringes 228 and 229 and the connection channels 273 and 274, arrange solenoid valves respectively between the connection channels 273 and 274 and the diluting fluid bottles (reaction auxiliary liquid diluting fluid bottle, cleaning liquid diluting fluid bottle), and dilute the remaining liquids by supplying the diluting fluid(s) from the reaction auxiliary liquid diluting fluid bottle and the cleaning liquid diluting fluid bottle to the reaction auxiliary liquid vessel 404 and the cleaning liquid vessel 405.

While the above embodiments have been explained by taking an example of a configuration in which the diluting fluid is supplied to the reaction auxiliary liquid vessel 404 and the cleaning liquid vessel 405 via the reaction auxiliary liquid supply system 251 and the cleaning liquid supply system 252, other configurations may also be employed. For example, it is possible to separately arrange supply systems for directly supplying the diluting fluid to the reaction auxiliary liquid vessel 404 and the cleaning liquid vessel 405 and drive the supply systems at times of dilution to supply the diluting fluid to the reaction auxiliary liquid vessel 404 and the cleaning liquid vessel 405.

While the above embodiments have been explained by taking an example of a configuration in which the cleaning liquid supply system 235 for the cleaning of the overflow part is provided separately from the cleaning liquid supply system 252 for supplying the cleaning liquid to the cleaning liquid vessel 405 and the cleaning tank 406, a channel branching off from a channel (e.g., the piping 410) connected to the cleaning liquid supply nozzle 403 and the cleaning tank 406 may be connected to the cleaning liquid supply channel 503 so that part of the cleaning liquid supplied to the cleaning tank 406 can be supplied to the cleaning liquid supply channel 503.

While the above embodiments have been explained by taking an example in which syringes are used as the liquid transfer means, it is also possible to use pumps instead of the syringes.

DESCRIPTION OF REFERENCE CHARACTERS 100 automatic analyzer
119 controller
200 detector
201 flow cell
202 suction nozzle
203 liquid transfer syringe
205 suction channel
251 reaction auxiliary liquid supply system (diluting fluid supply means)
252 cleaning liquid supply system (diluting fluid supply means, overflow part cleaning system)
262 reaction auxiliary liquid piping (diluting fluid supply means)
263 cleaning liquid piping (diluting fluid supply means, overflow part cleaning system)
264 drain channel (dumping part)
402 reaction auxiliary liquid nozzle (diluting fluid supply means)
403 cleaning liquid nozzle (diluting fluid supply means)
404 reaction auxiliary liquid vessel (liquid vessel)
405 cleaning liquid vessel (liquid vessel)
406 cleaning tank (dumping part)
502 overflow part
503 cleaning liquid supply channel (overflow part cleaning system)
504 cleaning liquid discharge outlet (overflow part cleaning system)
601 control valve
602 discharge outlet
603 discharge channel

The invention claimed is:

1. An automatic analyzer comprising:
a suction nozzle;
a suction syringe;
a channel which connects the suction nozzle and the suction syringe;
a flow cell which is arranged in the middle of the channel;
a detector for sample analysis which is arranged in the flow cell;
a reservoir unit having a drive mechanism to move the reservoir unit, and the reservoir unit separately holds a reaction vessel which stores a reaction solution, a liquid vessel which stores a liquid, and a cleaning tank;
a diluting fluid supplying nozzle which supplies a diluting fluid to the liquid vessel;
a diluting syringe connected to supply the diluting fluid to the diluting fluid supplying nozzle;
a dumping channel, connected to each of the liquid vessel and the cleaning tank, for disposing liquid remaining in the liquid vessel and the cleaning tank; and
a controller, connected to the suction syringe and the diluting syringe, that is programmed to move the drive mechanism to move the reservoir unit such that the reservoir unit rotates with respect to the suction nozzle and is driven upwards to the suction nozzle, and to drive the suction syringe to transfer the reaction solution in the reaction vessel into the flow cell via the suction nozzle, to drive the suction syringe to transfer the fluid in the liquid vessel into the flow cell via the suction nozzle, to drive the diluting syringe to supply the diluting fluid to the liquid vessel via the diluting fluid supplying nozzle to dilute the liquid remaining in the liquid vessel, to drive the suction syringe to suck the diluted liquid remaining in the liquid vessel via the suction nozzle, and then to drive the suction syringe to discharge the sucked remaining diluted liquid via the suction nozzle into the cleaning tank to be disposed via the dumping channel.

2. The automatic analyzer according to claim 1, wherein the controller is further programmed to drive the diluting fluid supplying nozzle to supply the diluting fluid to the liquid vessel in an amount which causes the remaining liquid to overflow from the liquid vessel to the dumping channel together with the diluting fluid.

3. The automatic analyzer according to claim 2, wherein the liquid vessel has an overflow part which connects the liquid vessel to the dumping channel.

4. The automatic analyzer according to claim 3, wherein the liquid vessel further comprises a cleaning liquid discharge opening for discharging a cleaning liquid to the overflow part.

5. The automatic analyzer according to claim 3, further comprising:
- a discharge outlet which is formed at the bottom of the liquid vessel;
- a discharge channel which connects the discharge outlet and the dumping channel; and
- a control valve which is arranged in the discharge channel,
- wherein the controller is further programmed to drive the diluting fluid supplying nozzle to supply the diluting fluid to the liquid vessel while also opening the control valve to cause the remaining liquid to be discharged from the liquid vessel through the discharge outlet together with the diluting fluid.

6. The automatic analyzer according to claim 1, wherein the suction nozzle is disposed at a fixed position above the reservoir unit.

7. A liquid discharging method for an automatic analyzer having:
- a suction nozzle,
- a suction syringe,
- a channel which connects the suction nozzle and the suction syringe,
- a flow cell which is arranged in the middle of the channel,
- a detector for sample analysis which is arranged in the flow cell,
- a reservoir unit having a drive mechanism to move the reservoir unit, and the reservoir unit separately holds a reaction vessel which stores a reaction solution, a liquid vessel which stores a liquid, and, a cleaning tank,
- a diluting fluid supplying nozzle which supplies a diluting fluid to the liquid vessel,
- a diluting syringe connected to supply the diluting fluid to the diluting fluid supplying nozzle, and
- a dumping channel, connected to each of the liquid vessel and the cleaning tank, for disposing liquid remaining in the liquid vessel and the cleaning tank, the method comprising:
- driving the suction syringe to transfer the reaction solution in the reaction vessel into the flow cell via the suction nozzle;
- driving the suction syringe to transfer the fluid in the liquid vessel into the flow cell via the suction nozzle;
- driving the diluting syringe to supply the diluting fluid to the liquid vessel via the diluting fluid supplying nozzle to dilute the liquid remaining in the liquid vessel;
- driving the suction syringe to suck the diluted liquid remaining in the liquid vessel via the suction nozzle;
- driving the suction syringe to discharge the sucked remaining diluted liquid via the suction nozzle into the cleaning tank and disposing of the sucked remaining diluted liquid in the cleaning tank via the dumping channel, and
- wherein the controller is further programmed to control the drive mechanism to move the reservoir unit such that the reservoir unit rotates with respect to the suction nozzle and is driven upwards to the suction nozzle.

* * * * *